United States Patent [19]
Cline

[11] Patent Number: 4,545,375
[45] Date of Patent: Oct. 8, 1985

[54] ELECTROSURGICAL INSTRUMENT
[75] Inventor: Albert L. Cline, Littleton, Colo.
[73] Assignee: Aspen Laboratories, Inc., Englewood, Colo.
[21] Appl. No.: 503,110
[22] Filed: Jun. 10, 1983
[51] Int. Cl.[4] .............................................. A61B 17/39
[52] U.S. Cl. ........................... 128/303.14; 128/303.17; 200/157; 200/302.2
[58] Field of Search ....................... 128/303.13, 303.14, 128/303.15, 303.16, 303.17, 303.18, 303.19, 800, 801; 219/230, 233, 234, 240; 200/157, 302.2

[56] References Cited
U.S. PATENT DOCUMENTS

| Re. 29,678 | 7/1978 | Antonini et al. | 206/571 |
|---|---|---|---|
| D. 249,549 | 9/1978 | Pike | D24/30 |
| 635,172 | 10/1899 | Meier . | |
| 2,457,153 | 12/1948 | Hubbell | 200/168 |
| 2,516,584 | 7/1950 | Parr | 200/138 |
| 2,727,116 | 12/1955 | Alfred et al. | 200/168 |
| 2,752,463 | 6/1956 | Staak | 200/168 |
| 2,877,324 | 3/1959 | Oshry | 200/168 |
| 3,126,467 | 3/1964 | Stevens, Jr. | 200/168 |
| 3,234,356 | 2/1966 | Babb | 219/233 |
| 3,371,179 | 2/1968 | Lohr | 200/153 |
| 3,383,487 | 5/1968 | Wiener | 200/168 |
| 3,541,488 | 11/1980 | Odson | 337/13 |
| 3,590,331 | 6/1971 | Kirsch | 317/112 |
| 3,651,297 | 3/1971 | Jones | 200/168 |
| 3,720,896 | 3/1973 | Beierlein | 335/206 |
| 3,732,390 | 5/1973 | Novak | 200/168 |
| 3,749,872 | 7/1973 | Foster | 200/166 |
| 3,801,766 | 4/1974 | Morrison, Jr. | 200/157 |
| 3,851,149 | 11/1974 | Daley | 219/528 |
| 3,911,241 | 10/1975 | Jarrard | 200/157 |
| 3,935,405 | 1/1976 | Auer | 200/52 |
| 4,034,761 | 7/1977 | Prater et al. | 128/303.14 |
| 4,034,762 | 7/1977 | Cosens et al. | 128/303.17 |
| 4,112,950 | 9/1978 | Pike | 128/303.14 |
| 4,170,234 | 10/1979 | Graham | 128/303.14 |
| 4,202,337 | 5/1980 | Hren et al. | 128/303.14 |
| 4,347,842 | 9/1982 | Beale | 128/276 |
| 4,427,006 | 1/1984 | Nottke | 128/303.14 |
| 4,443,935 | 4/1984 | Zamba | 128/303.17 |

FOREIGN PATENT DOCUMENTS 2094555 9/1982 United Kingdom ................ 200/157

OTHER PUBLICATIONS

Zimmer Product Profiler—"Handswitching Electrosurgical Pencils"— ©1982, (Profiler was released 10/15/82), Literature #82-049-0300-0085.
Aspen Advertisement—Aspen HAND-TROL Disposable Electrosurgical Pencil—Literature No. B-44-64— ©1980.

Primary Examiner—Lee S. Cohen
Attorney, Agent, or Firm—Margaret L. Geringer

[57] ABSTRACT

An electrosurgical instrument which includes an inner, insulated, elongated switching core integrally molded about an elongated main contact wire which extends continually throughout the core and extends from both the proximal and distal ends of the core. An electrode blade is connected to the distally extending portion of the main contact wire. Two selectively operable electrical contact switches are easily mounted on the core in a longitudinally spaced apart relation. Two windows are provided in the core, each exposing a portion of the main contact wire. Each window is respectively positioned beneath a portion of each of the contact switches so that one or the other of the switches may be selectively moved into engagement with the main contact wire. One of the switches provides a suitable electrical cutting signal to the electrode blade when in contact with the main contact wire, while the other switch provides a suitable electrical coagulation signal to the blade when in contact with the main contact wire.

A resilient tubular sleeve member may be mounted with a tight sealing fit over the inner core to encapsulate the switching core in order to prevent fluid from entering the switching area of the electrosurgical instrument.

15 Claims, 18 Drawing Figures

ELECTROSURGICAL INSTRUMENT

BACKGROUND OF THE INVENTION

The present invention relates generally to medical electronic apparatus and electrical switching devices, and more particularly to such a device especially suitable as an electrosurgical switching handpiece.

Various types of electrosurgical tools have been suggested and utilized in the medical field for a considerable period of time. Typically, in electrosurgery, a suitable electrical generator provides a high frequency or radio-frequency (RF) signal which is transmitted to a small surgical electrode having a thin knife-like tip to be applied to a patient. The patient sits or lies on a patient plate and is grounded thereto, with the plate being connected by a further conductor back to the generator. The relatively extremely small area of contact by the electrode with the patient provides an intense current in a highly localized area, producing a cutting action. The current passes through the patient's body to the patient plate where the area of contact is so great that no burning effect occurs to the patient.

For cutting purposes, the generator is activated to produce a continuous signal, typically a sinewave signal. However the same instrument may be used to apply to the wound after cutting in order to produce coagulation. For this purpose the generator may be selectively activated to produce a pulsing signal which produces the desired results. Switching means are available for the operator to selectively control an activating means for causing the generator to produce the desired type of current.

Suitable control switches may be mounted on the instrument panel of the generator to be operated by an assistant. This is generally considered to be unsatisfactory because of the delay involved in transmitting instructions. In other designs, foot operated switches are provided which may be controlled by the surgeon. However, this interferes with his mobility because he must stand in one place or move the foot switches about on the floor.

Various hand operated switching mechanisms for the dual purpose of cutting and coagulating tissue by the selective application of high frequency current of a selected type and power have become well known in the art. Such prior art devices include:

U.S. Pat. No. 3,801,766 to Morrison, Jr. discloses a hand-held electrical switching device for an electrosurgical instrument including a rectangularly shaped printed circuit board including three spaced apart electrical contacts. A spring contact member is disposed in electrical conducting engagement with the center contact and includes oppositely positioned contacts, each of which is adapted to be selectively engaged to one of the other contacts by means of a hand-activated rocker button. The Morrison patent is assigned to Valleylab, and while not described in this present patent, Valleylab markets a similar electrosurgical device which includes a sleeve member which is heat-shrunk over the printed circuit board to seal the circuit board from fluids. Such heat sealing requires the use of special equipment which is costly.

U.S. Pat. No. 3,911,241 to Jarrard shows an electrosurgical instrument including a switch with a pair of spaced contacts encased in a flexible housing. The space between the contacts allows actuation of the switch by manually squeezing the housing. More than one pair of spaced contacts may be incorporated in the housing. This reference discloses the use of a heat-shrinkable flexible covering to establish an environmental seal about the conductive elements.

U.S. Pat. No. 4,034,761 to Preter shows a hand-held electrosurgical switching assembly in which the switching member is mounted in the electrode handle for selectively moving one of the bowed portions of the resilient conductive member into contact with a wire wrap contact for actuation of the electrode blade in a desired operative mode.

U.S. Pat. Nos. 4,112,950 to Pike; 4,170,234 to Graham; and 4,202,337 to Hren illustrate additional hand-actuated electrosurgical instruments of interest.

It is also noted that some commercially available hand-actuated electrosurgical switching instruments utilize a flexible resilient sheath member externally around the housing and positioned to cover the switching buttons in an attempt to seal the switching mechanism from fluids. While this may keep fluids from entering through the cracks surrounding the actuating buttons, it does not prevent fluids from entering the housing via the cracks at the distal end of the instrument where the electrode blade enters the housing, or at the proximal end where the cable exits from the handpiece. Consequently, this means of sealing is generally not very effective.

Other commercially available hand-actuated electrosurgical switching instruments utilize several strategically placed "O"-rings, placed internally in the housing about the switching areas, relying on several seal points, in order to seal the switching mechanism from fluids.

OBJECTS OF THE INVENTION

A principle object of this invention is to provide a hand-actuated electrosurgical switching instrument which is simple and economical to manufacture and assemble, while at the same time, the unique construction of the instrument insures a highly reliable and precise instrument.

Another object of the invention is to provide such an instrument which is economically produced from suitable materials, so that it can be disposed after use, thus insuring a new sterile instrument for each operation.

A further object of the invention is to provide a hand-actuated electrosurgical switching instrument which includes a simple, yet effective means for sealing the switching mechanism from fluids.

A still further object of the invention is to provide such a sealed electrosurgical instrument which includes a main core portion for the switching mechanism, which may be fully encapsulated by a simple resilient sleeve so that the switching mechanism cannot be inadvertantly activated should the pencil be immersed in or splashed with a conductive fluid.

An even further object of the invention is to provide an electrosurgical switching mechanism which is simple to assemble.

SUMMARY OF THE INVENTION

The present invention accomplishes all of the above objects of invention. The present invention provides a hand-actuated electrosurgical switching instrument which is very simple to manufacture and assemble and yet provides a reliable switching mechanism. The instrument includes an insulated elongated inner core molded about an elongated main contact wire. The main contact wire extends throughout the length of the core and protrudes from both the distal and proximal ends of the core. An electrically conductive terminal connects to the distally protruding end of the main contact wire. This terminal electrically connects and secures a replaceable electrode blade assembly. The proximally protruding end of the main contact wire electrically connects to an RF wire which ultimately leads back through an insulated cable and a connector to an electrical generator or power source.

The inner core preferably includes two separate and selectively operable switch wires mounted thereon. The switches are longitudinally spaced apart from each other on the core, and may conveniently and easily snap into cooperating groove in the core. One end of each switch is aligned above and spaced apart from a respective window portion in the core. The window portion exposes a section of the main contact wire so that manual deflection of the switch wire will cause electrical contact with the main contact wire. Each switch wire is separately connected by a magnet wire via the insulated cable to the electrical power source. One wire is connected to an electrical signal suitable for cutting of tissue, while the other switch is connected to a different electrical signal suitable for coagulation of tissue. The electrosurgical generator supplies a pre-selected current to the electrode blade dependent upon which switch component is activated. Such cutting and coagulation signals are well known in the art and will not be further discussed herein.

The inner core is easily seated within the external housing of the instrument. A convenient selector means is mounted in the housing to provide externally activated deflection of the desired switch wire to provide the desired cutting or coagulation mode.

The inner core may be sealably encapsulated in a resilient sleeve member so that the switching mechanism cannot be inadvertently activated, should the instrument be immersed in or splashed with a conductive fluid. The selector means is operable through the sleeve to selectively activate the desired switch. The sleeve fits tightly over the elongated core in order to prevent such fluid from entering the switching area of the electrosurgical instrument. Additionally, this sealing protects the operator from RF current following the path of the conductive fluid from the internal circuitry to the user's hand.

The individual components of the present invention are designed to provide a highly dependable switching instrument while permitting simple, quick and economical assembly, so that the electrosurgical hand-actuated switching instrument may economically be provided as a disposable instrument in order to assure a sterile instrument for each operation.

BRIEF DESCRIPTION OF THE DRAWINGS

These features and objects of the invention, as well as others, will become apparent to those skilled in the art by referring to the accompanying drawings:

FIG. 10 is a top view of the core of the electrosurgical instrument of FIG. 2;

FIG. 11a is a side view of the core of FIG. 10;

FIG. 11b is an end view of the distal end of the core of FIG. 11a;

FIG. 11c is an end view of the proximal end of the core of FIG. 11a;

FIG. 12 is a bottom view of the core of FIG. 10;

DETAILED DESCRIPTION OF THE INVENTION

Figures 1, 2:
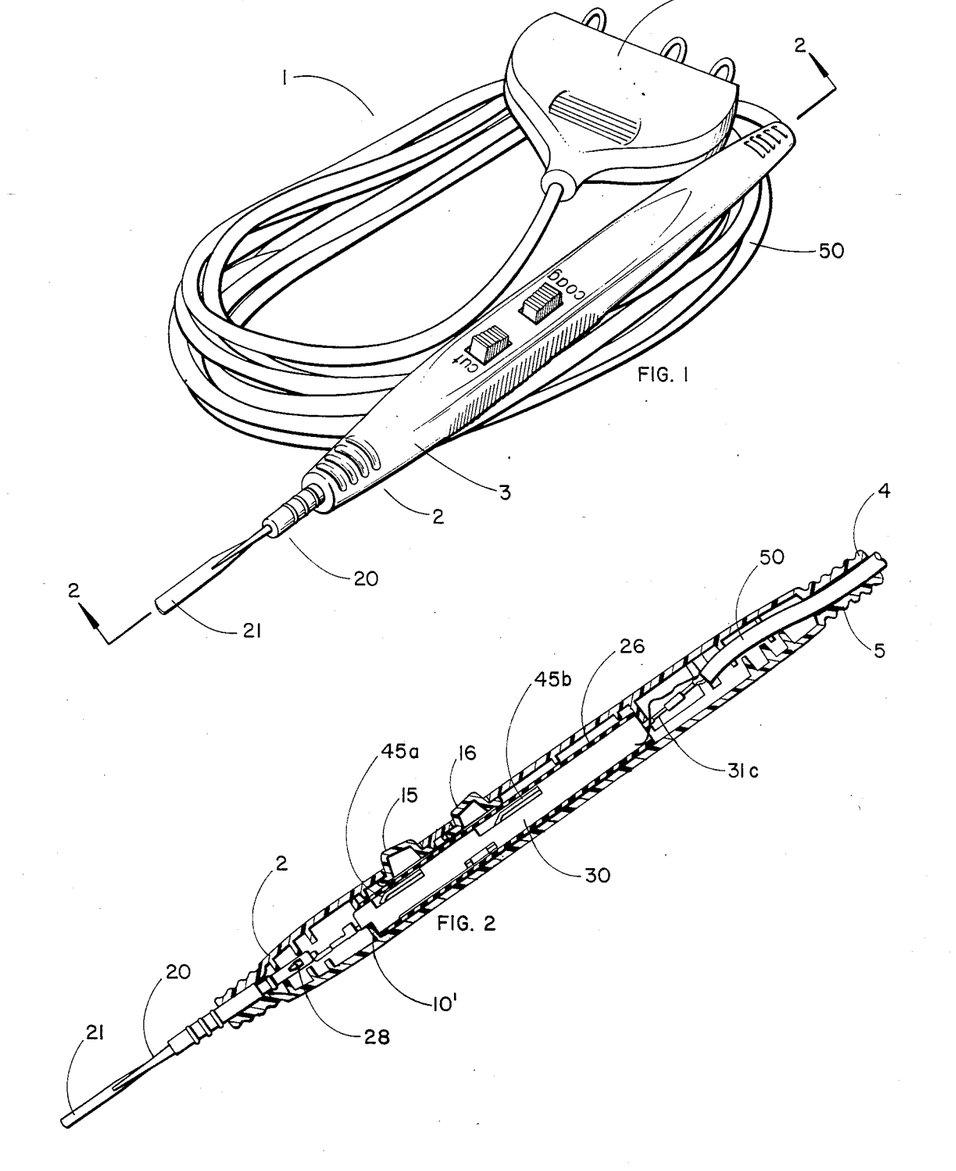
FIG. 1 is a perspective view of the electrosurgical instrument assembly according to the present invention.
FIG. 2 is a cross-sectional view taken through lines 2—2 of FIG. 1.

FIGS. 1-15 illustrate a particular embodiment of a hand-actuated electrosurgical switching mechanism according to the present invention. FIG. 1 illustrates an electrosurgical instrument assembly 1 comprising an electrosurgical handpiece instrument 2, a length of insulated cable 50 leading out of the electrosurgical instrument 2 at one end and into a connector 23 at the other end. The connector 23 attaches to a suitable electrical power supply (not shown).

Figures 5, 6:
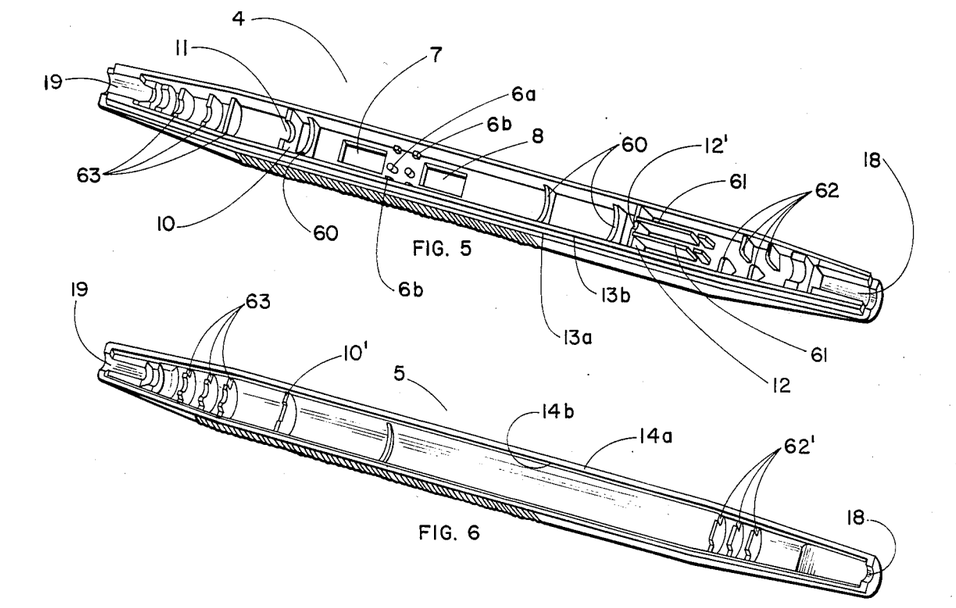
FIG. 5 is a perspective view of the interior of the top half of the housing of the electrosurgical instrument of FIG. 1.
FIG. 6 is a perspective view of the interior of the bottom half of the housing of the electrosurgical instrument of FIG. 1.

The electrosurgical instrument 2 includes an elongated external housing 3. The housing 3 may conveniently be manufactured in two halves, a top half 4 and a bottom half 5. The top half 4, as shown in FIG. 5, includes an outer ledge 13a and an inner ridge 13b along its elongated sides, while the mating bottom half 5, as shown in FIG. 6, includes an outer ridge 14a and an inner ledge 14b. The top half 4 of the housing 3 may then conveniently be fitted onto the bottom half 5 permitting the top inner ridge 13b to fit internally of and alongside the bottom outer ridge 14a. This permits the top inner ridge 13b to be aligned on top of the bottom inner ledge 14b and the top outer ledge to be aligned on top of the bottom outer ridge 14a forming a mating fitted closure of the two halves.

An elongated insulated structural switching core 30 is disposed within the housing 3, as shown in FIG. 2. The core 30 includes a distal end 40 and a proximal end 41 and an intermediate portion 42 disposed therebetween. A main electrical contact wire 31 is embedded within and extends throughout the insulated core 30, and extends distally and proximally out through the distal end 40 and proximal end 41, respectively. The structure of the core 30 is further illustrated in FIGS. 3 and 10-15. The portion of the main wire 31 embedded within the core 30 is designated as the intermediate portion of the main wire 31b, while the distally extending portion is 31a and the proximally extending portion is 31c.

Figure 16:
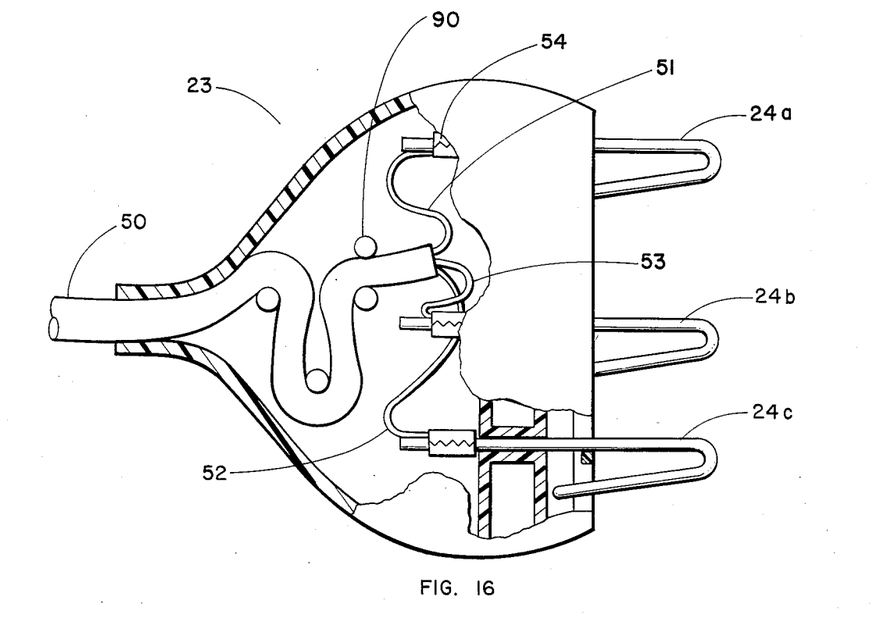
FIG. 16 is a top view, in partial cross-section, of the connector.

The proximal end 31c of the main contact wire connects back to a radio-frequency power source via the RF wire 51 which is secured in electrical contact to proximal main wire 31c by a suitable splice 54. The RF wire 51 may conveniently be comprised of multiple strands of copper wire. The RF wire leads into an insulated cable 50 which leads out of the handpiece 2 through the proximal opening 18 in the housing 3. The RF wire continues into the connector 23 and is electrically connected by a splice 54 to one of the spring contacts 24a in the connector 23, as shown in FIG. 16. The spring contacts 24 of the connector plug into the power source. Such connectors 23 are well known in the art, and any suitable connector may be used for connecting the cable 50 to the power source to provide the electrical energy.

The distal end 31a of the main contact wire is connected to the electrode blade assembly via an electrically conductive terminal 28. One end of the terminal 28 may be crimped onto the distal end 31a, while the other end of the terminal 28 has an opening for accepting and securing, by tight friction fit, the electrode blade assembly 20 in electrical contact. The electrode blade assembly 20 may be removable. Thus, the blade portion 21 is electrically connected through the terminal 28 to the main contact wire 31, and then to the RF wire 51. The electrode blade assembly 20 extends through the distal hole 19 in the housing 3. The electrode blade assembly includes an external insulated covering over the midportion of the assembly.

At least one electrical contact switch is mounted on the intermediate core portion 42. In the embodiment shown, two electrical contact switches 45 are shown, one 45a for activating the cutting mode and the other 45b for activating the coagulation mode. The intermediate core 42 includes a window means 39 which exposes a portion of the intermediate main contact wire 31b. The window means 39 includes a window 39a located in proximity to mounted switch 45a, and a window 39b located in proximity to mounted switch 45b.

A selector means for activating either the cutting or coagulation mode is also provided which is movably mounted relative to the housing 3. In the embodiment shown, the selector means is comprised of two selector buttons 15 and 16. Contact switch 45a is positioned on the intermediate core 42 so as to extend between the cut selector button 15 and window 39a, while contact switch 45b is positioned on intermediate core 42 so as to extend between the coagulation selector button 16 and window 39b.

Figure 3:
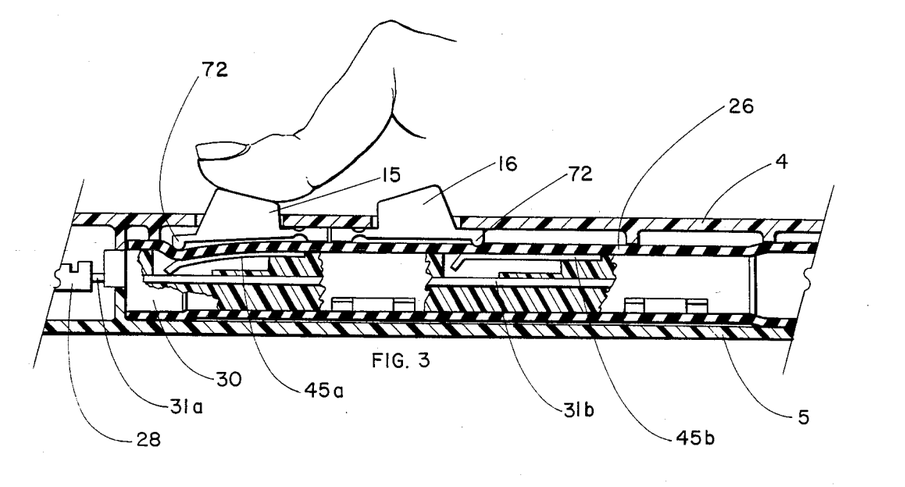
FIG. 3 is an enlarged view of the mid-portion of FIG. 2.

Selector button 15 may be selectively, manually depressed, as shown in FIG. 3, thus contacting and deflecting switch 45a, causing switch 45a to make electrical contact with the intermediate portion 31b of the main contact wire through window 39a. Contact switch 45a is electrically connected to appropriate cutting circuitry in the power source so that when switch 45a contacts the main contact wire 31, which is connected by the RF wire 51 back to the power source, this completes the signal circuit which causes the power source to produce the desired electrical signal to effect cutting at the blade 21.

Selector button 16 also may be selectively, manually depressed to contact and thus deflect switch 45b, causing portion 31b of the main contact wire through window 39a. Contact switch 45b is electrically connected to appropriate coagulation circuitry in the power source so that when switch 45b contacts the main contact wire 31, which is connected by the RF wire 51 back to the power source, this completes the signal circuit which causes the power source to produce the desired electrical signal to effect coagulation at the blade 21.

Each contact switch 45 is a thin, elongated electrically conductive wire. The contact switches 45 each conveniently snap-fit into a corresponding groove 35 suitably shaped for securing said switch to the intermediate portion of the core 42.

The core 30 may be substantially cylindrical in shape. The intermediate core 42 includes a contact cut out portion 38a positioned on the side of core directly beneath the cutting selector button 15. Window 39a is positioned in this contact cut out portion 38a and is positioned so that contact switch 45a may be deflected by manual depression of the cut button 15 and caused to contact the main contact wire 31 through the window 39a. The intermediate core 42 also includes an insulated cut out portion 43a spaced longitudinally apart from and on the opposite side of the core 30 from contact cut out 38a, as shown in FIGS. 10-15. A groove 35a for contact switch 45a is positioned between cut out 38a and cut out 43a. The groove 35a includes a first leg 36a and a second groove 36a' and an interconnecting portion 37a therebetween. The interconnecting portion 37a has two ends and is semi-circular in shape, following the outer shape of the cylindrical core 30. The first leg 36a of the groove extends from one end of the circular portion 37a to the contact cut portion 38a. The second leg 36a' extends from the other end of the circular portion 37a to the insulated cut out portion 43a.

The switch wire 45 has a corresponding shape to the continuous groove 35 enabling the switch wire 45 to be snapped in the groove 35 and thus mounted about the core 30. The switch wire 45 is shown separately in FIG. 8, and is shown in place on the core 30 in FIGS. 14 and 15. Switch wire 45a includes a first elongated leg 46a and a second elongated leg 46a' and a circular connecting portion therebetween. Switch leg 46a snaps into groove leg 36a, while the switch connecting portion 47a snaps into groove connecting portion 37a and switch leg 46a' snaps into groove leg 36a'. Preferably, as shown, the legs of the switch and the legs of the groove, form a right angle with the semi-circular curved portion of the switch and groove, respectively.

With the switch 45 in place, at least leg 46a of the switch 45a extends beyond its corresponding leg 36a of the groove 35a, so that the leg overhangs into the cut out area 38a. Leg 46a extends to enable it to deflect upon manual depression of the selector button 15. The free end of leg 46a is positioned above the window 39a, as shown in FIG. 3, so that upon depression of button 15, the end of leg 46a will make contact with the main switch wire 31. The switch may advantageously be symmetrical in shape. The advantage of the symmetry will be later described. Each leg 46 may include a bent tip 48 which is angled toward the main contact wire 31 which is preferably centrally located within the core 30. The angled tip 48 of leg 46a', if deflected, is positioned to contact insulated material. Thus, if for some reason it would be deflected, no electrical contact would occur.

The portion of the core 30 between the contact cut out 38a and the insulated cut out 43a, which includes the S-shaped groove, supports the switch 45a to prevent rocking of the switch wire. The S-shape of the groove and wire also prevents rotation of the switch wire 45.

Figures 10, 11A, 11B, 11C, 12:
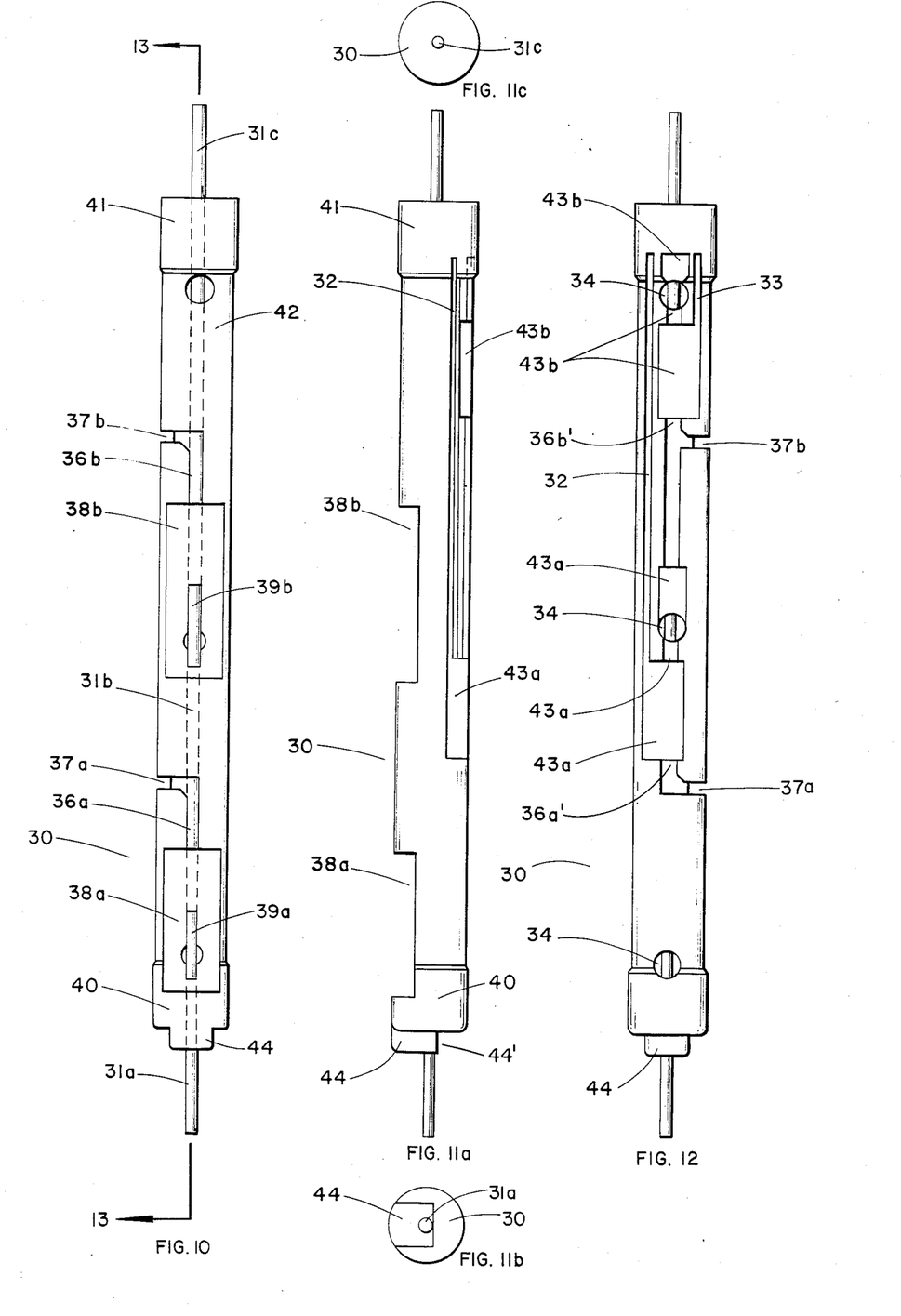
Figure 13:
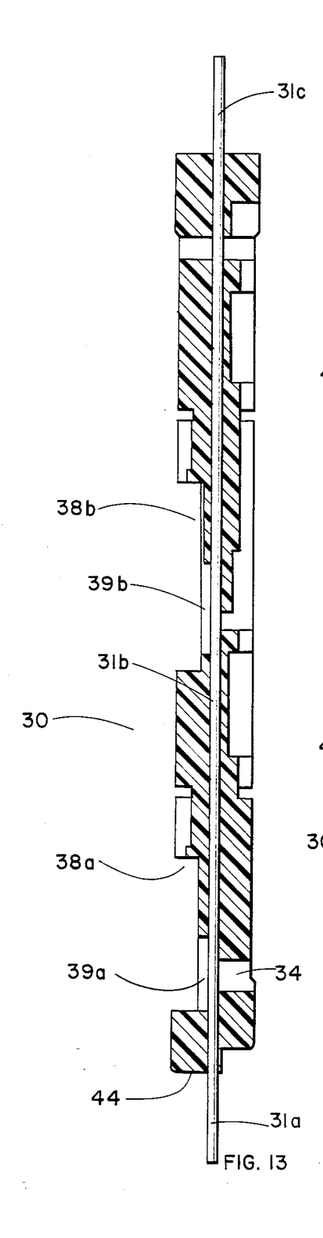
FIG. 13 is a cross-sectional view of the core of FIG. 10 taken along lines 13—13.

Once switch 45a is mounted on the core 30, leg 46a overhangs into cut out 38a, while leg 46a' overhangs into cut out 43a. It is not essential that the cut outs 38a and 43a be any particular shape. Cut out 38a, as shown in FIGS. 10 and 11a, may conveniently be a substantially rectangular cut out, while cut out 43a, as shown in FIGS. 12 and 13, includes a first substantially rectangular portion with a short channel connecting to a second smaller, substantially rectangular portion An elongated cut out channel 32 extends from the first rectangular portion of 43a and runs toward the proximal end 41 of the core 30.

Figure 15:
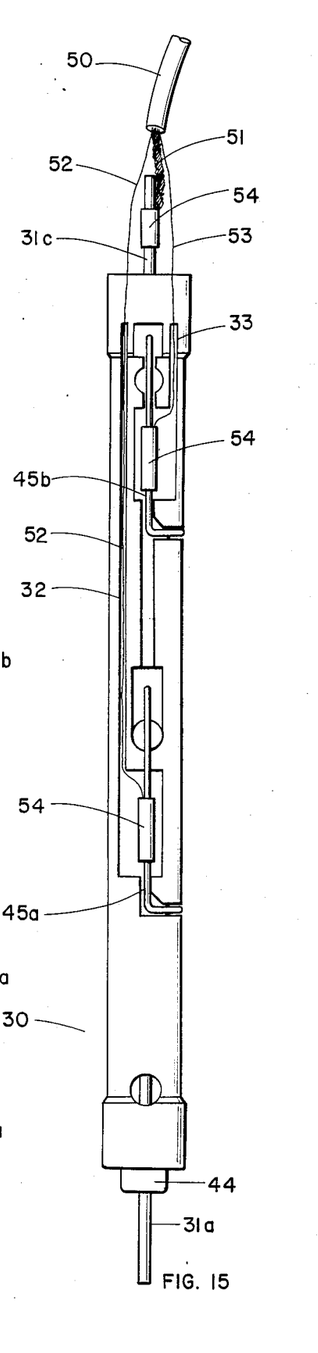
FIG. 15 is a bottom view of the core of FIG. 14.

A single strand magnet wire 52 is secured in electrical contact to leg 46a' by a splice 54. The splice is located in the first rectangular portion of cut out 43a. The wire 52 follows the length of channel 32, as shown in FIG. 15. The wire 52 then leads into the insulated cable 50 which leads out of the handpiece 2 into connector 23 where it is electrically connected by a splice 54 to another of the spring contacts 24c in the connector 23. The magnet wire 52 has a thin insulated coating over the single stranded wire. Preferably, the splices 54 may have serrations on the inside to displace the insulation on either end of wire 52, thus assuring a good electrical contact with switch leg 46a' and with spring contact 24c. Alternatively, if the splices 54 do not include such internal serrations, both ends of wire 52 may be stripped of the thin insulated coating where the splices 54 are applied, thus assuring good electrical contact.

When the connector 23 is plugged into a suitable power supply, and the cutting button 15 is manually depressed to cause leg 46a to contact the main contact wire 31, this electrically interconnects the switch wire 45a, which is electrically connected via magnet wire 52 to a suitable cutting signal in the power source with the main contact wire 31 which is connected to the power source via the RF wire 51, thus completing the electrical circuit, causing the appropriate electrical cutting signal to flow to cutting blade 21.

Figure 14:
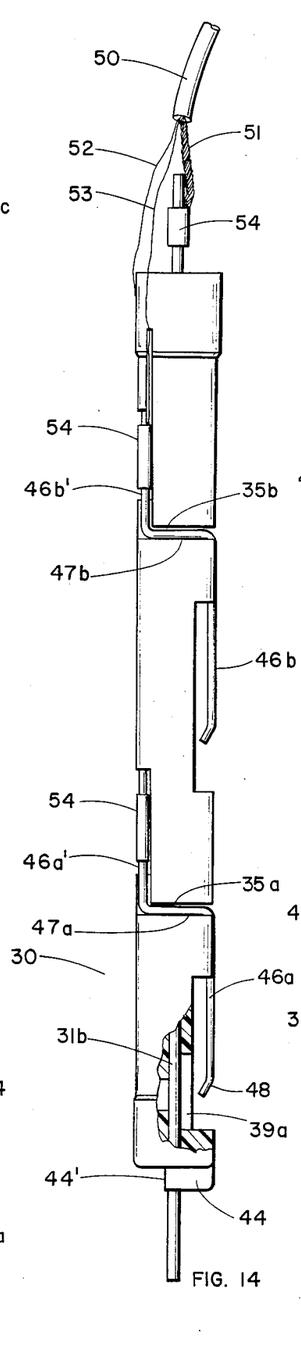
FIG. 14 is a side view of the opposite side of the core of FIG. 11a, including a partial cross-section of the distal portion of the core.

The intermediate core 42 includes a second contact cut out portion 38b positioned beneath the coagulation selector button 16, proximally to the first contact cut out portion 38a. Window 39b is positioned in cut out 38b so that contact switch 45b may be deflected by manual depression of the coagulation button 16, and caused to contact the main contact wire 31 through window 39b. A second insulated cut out portion 43b is also provided and is spaced longitudinally apart from and on the opposite side of the core 30 from cut out 38b. A second groove 35b is positioned between cut outs 38b and 43b similar to the first groove discussed above, which is positioned between cut outs 38a and 43a. The second groove is comprised of legs 36b and 36b' and connecting portion 37b for accepting switch wire 45b. Switch wire 45b is similar to switch wire 45a, previously discussed, and includes legs 46b and 46b', connecting portion 47b and bent tips 48. Switch wire 45b is snapped into groove 35b, as shown in FIGS. 14 and 15.

As with switch 45a, once switch 45b is mounted on the core 30, leg 46b overhangs into cut out 38b and is positioned above and spaced apart from window 39b. Leg 46b' overhangs into cut out 43b. Cut outs 38b and 43b are shaped similarly to cut outs 38a and 43a. An elongated cut out channel 33 extends from the first rectangular portion of 43b and runs toward the proximal end 41 of the core 30, as shown in FIG. 12.

A single strand magnet wire 53 is secured in electrical contact to leg 46b' of switch wire 45b by splice 54. The wire 53 follows the length of channel 33, as shown in FIG. 15. The wire 53 then leads into the insulated cable 50 which leads out of the handpiece 2 into connector 23 where it is electrically connected by a splice 54 to another of the spring contacts 24b in the connector 23.

Like magnet wire 52, magnet wire 53 also has a thin insulated coating over the single strand wire. As with wire 52, the splices 54 preferably have serrations on the inside to displace the insulation on either end of wire 53, thus assuring a good electrical contact with switch leg 46b' and with spring contact 24b. If the splices 54 do not include such internal serrations, both ends of wire 53 may be stripped of the thin insulated coating where splices 54 are applied, thus assuring good electrical contact.

When the connector 23 is plugged into a suitable power supply, and the coagulation button 16 is manually depressed to cause leg 46b to contact the main contact wire 31, this electrically interconnects switch wire 45b, which is electrically connected via magnet wire 53 to a suitable coagulation signal in the power source, with the main contact wire 31 which is connected to the power source via the RF wire 51, thus completing the electrical circuit, causing the appropriate electrical coagulation signal to flow to cutting blade 21.

Figure 4:
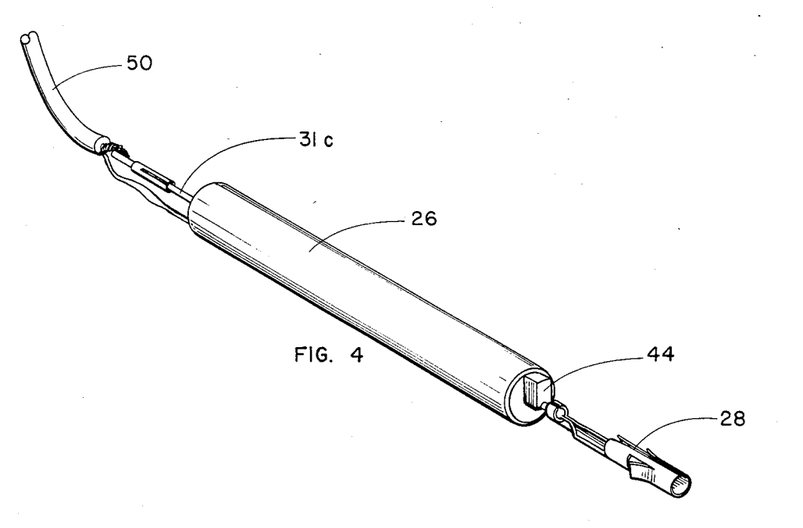
FIG. 4 is a perspective view of the inner core, including the resilient sealing sleeve member of the electrosurgical instrument of FIG. 2.

A resilient tubular sleeve member 26, as shown in FIGS. 2-4, may be mounted with a tight sealing fit over the inner core 30 to encapsulate the switching core 30 in order to prevent fluid from entering the switching area of the electrical instrument 2. The sleeve member 26 is made of a suitable fluid resistent material.

The core 30 includes distal and proximal members 40 and 41, respectively, with the intermediate core portion 42 connecting therebetween. The core 30 may be substantially cylindrical, although other shapes are suitable. When utilizing the sealing sleeve 26, the circumference (in the case of a cylindrical core, the outer diameter) of the distal and proximal core portions 40 and 41 are equal to or greater than the outer circumference (or outer diameter) of the intermediate core portion 42. The intermediate core portion 42 includes the switch contacts 45a and 45b and the electrical contact areas. The sleeve 26 has an inner circumference less than the outer circumference of the distal and proximal ends of core 30. The sleeve extends from at least a portion of said distal end 40 to at least a portion of the proximal end 41. Preferably, as shown in FIGS. 2 and 4, the sleeve 26 covers all of the distal and proximal ends 40 and 41 and is substantially flush with the distal and proximal end faces of the core 30. The sleeve 26 has a suitable length to cover the length of the core.

The sleeve 26 creates a tight sealing engagement with end 40 and 41 preventing any conductive fluid from entering the intermediate or switching area 42 of the core 30. Preferably, wires 52 and 53 run parallel to the length of core 30 and pass between the proximal end of the sleeve 26 and the proximal end 41 of the core 30, so that the sleeve 26 also seals the entry point of the wires 52 and 53 into the intermediate, switching portion 42 of the core 30. Since the switching core is fully encapsulated in the resilient sleeve 26, the switching mechanism cannot be inadvertently activated, should the pencil be immersed in or splashed with a conductive fluid. Additionally, this sealing protects the operator from RF current following the path of the conductive fluid from the internal circuitry to the user's hand.

In a particularly advantageous embodiment of the invention, the distal and proximal end 40 and 41 may have a diameter of approximately 0.265" (6.73 mm) while the inner diameter of the sleeve 26 when relaxed or not stretched may be approximately 0.250" (6.35 mm) providing a difference of about 0.015" (0.38 mm) between the diameters, thus creating a tight sealing fit of the sleeve when it is mounted about the core 30.

The selector buttons 15 and 16 which are movably mounted in the top half 4 of the housing 3, are operable through the sleeve 26 to selectively deflect the contact switches 45a and 45b, respectively, into electrical contact with the main contact wire 31. The sleeve 26 is formed of a material that is sufficiently pliable so that the switch, such as switch 45a will be deflected by the operator pressing a selector button, such as 15, which in turn presses on the sleeve 26 to deflect the switch 45a into contact with main contact wire 31.

Figure 7:
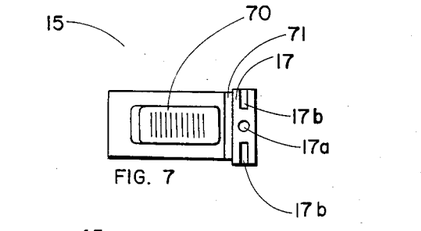
FIG. 7 is a top plan view of a selector button of the electrosurgical instrument of FIG. 1.
Figure 8:
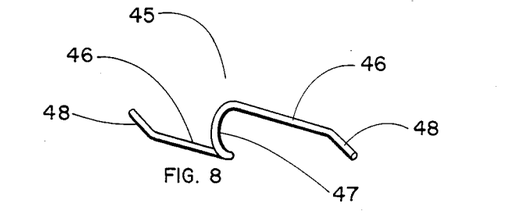
FIG. 8 is a perspective view of a switch wire of the electrosurgical instrument of FIG. 2.
Figure 9:
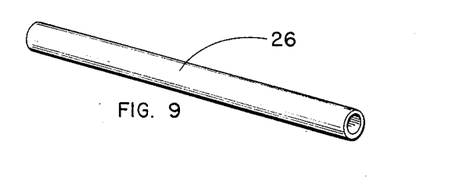
FIG. 9 is a perspective view of the sleeve member of the electrosurgical instrument of FIG. 2.

As shown in FIG. 5, two apertures 7 and 8 are provided in the top half 4 of housing 3 for mounting buttons 15 and 16, respectively. FIGS. 2 and 3 illustrate buttons 15 and 16 positioned in the housing 3. Buttons 15 and 16 are identical in shape, but are positioned in the housing 3 as mirror images of each other. The button 15, as shown in FIG. 7, includes a main protruding portion 70 for extending through aperture 7 from the inside of the housing 3 to the outside of the housing 3. The button 15 further includes an integral hinge member 71 and a locating means 17. The hinge 71 allows deflection of the button 15 when manually depressed, while locating means 17 secures the button to the housing 3. The locating means 17, as shown, includes a center hole 17a and two side slots 17b for fitting onto corresponding center circular protrusion 6a and protruding side ridges 6b on the inner top surface of the top half 4 of the housing 3. As shown in FIGS. 2 and 3, the sleeve 26 which is supported by the outer surface of the intermediate core 42, in turn supports the locating means 17 of the buttons 15 and 16 to further hold them securely in the housing 3. Also, protruding rib 72, as shown in FIG. 3, may be provided on the buttons 15 and 16 to aid in deflection of switches 45a and b.

The housing 3 further includes a series of panels on the inner surfaces of the top half 4 and bottom half 5 of the housing 3, as shown in FIGS. 5 and 6. The top half 4 includes a distally located main core support panel 10 and a proximally located core support panel 12. Panel 10 supports an alignment nub 44 which extends from the distal end 40 of the core 30. The sleeve 26 does not extend to cover the nub 44. Nub 44, shown in FIGS. 11a and b extends from the upper portion of the core 30 and fits into and is supported by a corresponding slot 11 in panel 10. The mating relation of the nub 44 to the slot 11 ensures the proper orientation of core 30 in housing 3 so that legs 46a and 46b are aligned appropriately beneath buttons 15 and 16, respectively. Panel 12 includes a very small slot 12' for supporting the proximally extending portion 31c of the main contact wire. The lower half 5 of the housing 3 includes a panel 10' which aligns with panel 10 and supports the lower surface 44' of nub 44, as shown in FIG. 2. Both halves 4 and 5 include additional core support panels 60, as shown in FIGS. 5 and 6 to additionally support the core so it is securely located in position to keep switches 45 in alignment with the selector means and to prevent the core from sliding, rotating or rattling around inside the housing 3.

Halves 4 and 5 both include panels 63 at the distal end of the housing 3 to support and locate terminal 28 securely in the housing 3. The top half 4 includes longitudinal panels 61 to provide a channel for the proximally extending end 31c of the main contact wire 31. The top half 4 further includes staggered partially extending panels 62 for dressing the cable 50 through to tightly hold cable 50, while bottom half 5 includes fully extending panels 62' to press against and further hold cable 50 securely in place.

Electrosurgical instrument 2 may be simply manufactured. The core 30 may be conveniently and simply molded about main contact wire 31. The core may be molded out of any suitable, insulated material, such as polystyrene. Holes 34 through the core 30 are provided as wire support features to aid in the molding of the core 30. The holes 34 are positioned so that no electrical contact could inadvertently occur through the holes 34 to the main contact wire 31. Holes 34 are located in the intermediate core 42, so that when sleeve 26 is used, holes 34 are in the sealed area.

The main contact wire 31 and contact switches 45a and 45b may be manufactured from a suitable conductive material, such as phosphor bronze with a nickel plate finish. Wire 31 is simply cut off from straight stock, while switches 45 are cut to length and then formed into the desired shape from straight stock.

The multi-strand wire 51 may typically utilize suitable copper wire. Likewise, magnet wires 52 and 53 typically each utilize a single strand of copper wire. Wires 52 and 53 utilize a thin film insulated coating, such as varnish or laquer. Wires 52 and 53 are insulated to prevent shorting to the RF wire 51 which could cause premature switch activation. The multiple copper wires forming the RF wire 51 are not insulated except as covered by the cable 50.

The insulated cable 50 is molded about the RF wires 51 and the magnet wires 52 and 53. Cable 50 is made of a suitable insulated material, such as poly vinyl chloride (PVC).

The splices 54 may be made out of a conductive material, such as brass. The splices band wires 51, 52 and 53 to the main contact wire 31 or switches 45a or 45b, respectively. Such splice 54 are also used to band wires 51, 53 and 52 to spring contacts 24a, 24b, and 24c, respectively.

The sleeve 26 may simply be a hollow piece of resilient tubing formed from a suitable resilient and fluid resistant material, such as latex. The sleeve 26 may have a thickness of about 0.032" (0.81 mm).

Preferably, buttons 15 and 16, as well as the top and bottom housing halves 4 and 5 are each integrally molded parts. They may be molded from a suitable insulated material. For example, the buttons are conveniently molded from polypropylene, and the housing halves may be made of polystyrene.

The terminal 28 is made of a conductive material, such as tin plated brass. The electrode blade assembly 20 includes a conductive proximal portion which is fitted securely into terminal 28 as shown in FIG. 2. This conductive proximal portion extends distally to the conductive blade 21. The mid-portion of the electrode assembly 20 includes an insulated portion molded about the continuous conductive portion of the assembly 20. This provides an insulated portion for gripping to manually insert and remove the blade assembly 20 from the handpiece 2. The insulated portion of assembly 20 may be made of a suitable material, such as polystyrene, while the conductive portion may be made of stainless steel. The blade 21 may also be conveniently made of stainless steel. The blade 21 may or may not be integrally manufactured with the remainder of the conductive portion of the assembly 21.

The assembly of the electrosurgical handpiece assembly 1 is very simple. The cable 50 is cut to length and the insulation is stripped at both ends to expose the wires 50, 51 and 52. Wires 50, 51 and 52 are cut to their predetermined lengths. Wires 51, 52 and 53 may be easily banded to spring contacts 24a, 24c and 24b, respectively with splices 54. See FIG. 16. Preferably, the splices 54 include serrations on the inside to displace the thin insulated coating on magnet wires 52 and 53 to assure good electrical contact. Magnet wires 52 and 53 are then banded to switches 45a and 45b with splices 54. Since the switches 45 are symmetrical the assembler does not have to decide which leg 46 to splice the magnet wire to. Once the magnet wire is spliced to one switch leg or the other, this determines the orientation of how the switch 45 will be positioned on the core 30 in an appropriate groove 35 so that the splice 54 is located in the appropriate insulated cut out 43. The magnet wires 52 and 53 may be color coded, and one magnet wire is cut to a longer length than the other. For example, wire 52 which leads to the cut switch 45a may be green, while the other wire 53 which leads to the coagulation switch 45b may be red. The green cut wire 52 is cut to a predetermined longer length allowing it to extend up to its proper location so cut switch 45a may be located beneath cut button 15. The shorter length of red coagulation wire 53 allows switch 45b to be located on core 30 only beneath coagulation button 16.

The terminal 28 is then crimped to the distal main contact wire 31a. The RF wire 51 is then spliced to the proximal main contact wire 31c. The splicing is simply done by taking a splice 54 and wrapping it around the wire 31c and the end of RF wire 51 and crimping or banding them together. Switches 45a and 45b are then snapped into their respective grooves 35a and 35b on core 30. Magnet wires 52 and 53 are then pressed into channels 32 and 33, respectively.

After all the electrical wires and switches are in place, the sleeve 26 is ready to be assembled. About ⅛" of one end of the sleeve 26 is dipped in a lubricant, such as alcohol. This lubricated end is then easily slipped onto the distal end 40 of core 30. Compressed air is then used to shoot a jet of air through the sleeve 26 which slightly inflates the sleeve 26, so it slides easily onto the core 30, making sure sleeve 26 is flush with the distal and proximal faces of portions 40 and 41 of the core 30. This provides a simple, yet effective means of mounting the sleeve 26 over the core 30 without requiring the use of expensive, and time consuming equipment, such as may be needed if heat sealing were to be used for sealing the switching mechanism.

The three spring contacts 24a, 24b and 24c are then installed in one half of the connector housing in predetermined positions, as shown in FIG. 16. The spring contacts are spaced so that connector 23 can only fit one way into the power source, insuring that the magnet wires 52 and 53 and the RF wire 51 will be connected to the proper circuitry in the power source. The cable 50 is dressed through the retaining bosses 90, as shown. The other half of connector 23 is placed on top of the first half so that cable 50 extends out of the connector 23, as shown. The two halves of the connector 23 are then ultra-sonically welded together.

The switch buttons 15 and 16 are then installed into the top half 4 of housing 3 in apertures 7 and 8, respectively by press fitting the holes and slots 17a and 17b onto corresponding circular protrusion 6a and ridges 6b. The switch core assembly is then placed into the top half 4 of housing 3 making sure alignment nub 44 is properly aligned in slot 11 on support panel 10. The cable 50 is then dressed thru panels 62 in top half 4. The bottom half 5 is then placed onto the top half 4, and the halves ultra-sonically welded together.

An electrode blade assembly 20 may be inserted into terminal 28 either before top 4 and bottom 5 of housing 3 are put together, or anytime after by inserting the proximal end of the assembly 20 through distal opening 19 in the housing 3. The electrode blade assembly is easily removable in case a new blade assembly or other style electrode is desired.

The invention described herein is an electrosurgical instrument assembly which is easily manufactured and assembled from inexpensive materials, and thus suitable as a disposable instrument, yet it is a unique, well constructed instrument insuring a highly reliable and precise electrosurgical switching instrument. While this invention has been described and exemplified in terms of a particularly advantageous embodiment, those skilled in the art can appreciate that modifications can be made without departing from the spirit and scope of this invention.

I claim:

1. An electrosurgical instrument for selectively providing electrical energy from an electrosurgical generator to an electrode blade for cutting, coagulation and the like comprising:

a housing;

a selector means movably mounted relative to the housing;

an inner insulated, elongated core member disposed within the housing, having a first end, a second end and an intermediate portion therebetween;

a main electrical contact wire embedded within and extending throughout said inner core member and extending distally out of said first end and proximally out of said second end, said intermediate portion of said inner core member including at least one window exposing the main contact wire;

a means for connecting the proximally extending portion of said main contact wire to electrical energy;

an electrode blade in electrical contact with said distally extending portion of the main contact wire, said blade extending outwardly from the housing;

at least one electrical contact switch mounted on the intermediate portion of said inner core member; and, a means for connecting said at least one switch to electrical energy, said at least one switch extending between said selector means and said at least one window and spaced apart from said window, said selector means operatively moving the at least one electrical contact switch as desired by an operator, to electrically contact the main contact wire exposed through said at least one window, effecting an electrical interconnection between the electrode blade, the main contact wire and the contact switch in electrical contact with said main contact wire.

2. The electrosurgical instrument of claim 1 wherein both of said first and second ends of the core member have an outer circumference and wherein said instrument further includes a relilient tubular sleeve member, made of a fluid resistant material, said sleeve member having an inner circumference less then the outer circumference of the first and second ends of said inner core member, said sleeve member mounted over said inner core member, from at least a portion of said first end to at least a portion of said second end, and in tight sealing engagement with said portions of the first and second ends, said at least one switch located within the sleeve member, and said selector means operating through said sleeve member to move the at least one switch into electrical contact with the main contact wire, as desired by the operator.

3. The electrosurgical instrument of claim 1 wherein said intermediate portion of the inner core member includes two spaced apart windows, each exposing a portion of the main contact wire, and further includes two electrical contact switches mounted on said intermediate portion, each respectively extending between the selector means and one of the windows.

4. The electrosurgical instrument of claim 3 wherein said housing includes a pair of apertures and the selector means includes a pair of buttons extending outward of the housing through a respective aperture, and wherein the electrosurgical instrument includes a locating means for holding the buttons in the pair of apertures.

5. The electrosurgical instrument of claim 1 wherein said housing includes in its interior at least a pair of spaced apart panel members supporting the inner core member in proper location inside the housing.

6. The electrosurgical instrument of claim 5 wherein the inner core member includes an alignment nub extending from one end thereof, and one of said spaced panel members includes a corresponding slot accepting said nub which aids in orienting the core member in a proper position in the housing.

7. The electrosurgical instrument of claim 1 wherein said core member is substantially cylindrical.

8. The electrosurgical instrument of claim 1 wherein said at least one electrical contact switch is a thin elongated electrically conductive wire and wherein said core member includes at least one corresponding groove suitably shaped for securing said switch to the core member by a snap-fit into said groove.

9. The electrosurgical instrument of claim 8 wherein said core member includes at least one contact cut out portion on the side of the core member positioned beneath the selector means and at least one insulated cut out portion spaced longitudinally apart and on the opposite side of the core member from the contact cut out, and wherein said at least one window is located in said contact cut out portion, and wherein said groove in the core member has a first and second leg and an interconnecting portion therebetween, and positioned between said at least one contact cut out portion and said at least one insulated cut out portion, the first leg extending longitudinally from one end of the interconnecting portion to the contact cut out portion and the second leg extending longitudinally from the other end to the insulated cut out portion, and wherein said at least one switch wire includes first and second elongated legs and a connecting portion therebetween, corresponding to the legs and interconnecting portion of the groove, said switch wire secured into said groove by a snap-fit and wherein the first switch leg fits into and extends out of the leg of the groove which leads to the contact cut out and overhangs into the contact cut out such that the end of said first switch leg is positioned above said window and spaced apart from the main contact wire, and wherein said selector means is positioned above said first switch leg and may be operatively moved to effect deflection of said first switch leg causing the end of said first switch leg to electrically contact the main contact wire through the window.

10. The electrosurgical instrument of claim 9 wherein said second switch leg fits into and extends out of the leg of the groove which leads to the insulated cut out and overhangs into the insulated cut out such that the end of said second switch leg is positioned above an insulated portion of the core member, whereby any deflection of said second switch leg that may occur would cause the end of said second switch leg to contact an insulated area, and thereby not effect any electrical connection.

11. The electrosurgical instrument of claim 9 wherein said core member is substantially cylindrical, and said interconnecting groove portion is semi-circular in shape and said connecting portion of the switch wire has a corresponding semi-circular shape.

12. The electrosurgical instrument of claim 11 wherein the free ends of each switch leg are bent toward the axis of the semi-circular portion of the switch.

13. The electrosurgical instrument of claim 9 wherein said switch is symmetrical.

14. The electrosurgical instrument of claim 9 wherein said inner core member includes two sets of contact and insulated cut outs spaced longitudinally apart from each other on the core member, and wherein each said contact cut out portion respectively includes a window therein, each window exposing a portion of the main contact wire, and each set including such a two-legged switch snapped into a corresponding groove on the core member such that the first switch leg of each respective two-legged switch is positioned above the respective window and spaced apart from the main contact wire and wherein the selector means is operatively positioned above each respective first leg.

15. The electrosurgical instrument of claim 14 wherein said means for connecting the at least one switch to electrical energy includes a separate magnet wire individually connected at one end to each switch, and the other end of each magnet wire adapted for connection to electrical energy, said inner core member further including a pair of longitudinal slots, each respectively receiving one of said magnet wires as they extend along the longitudinal direction of the core member.

* * * * *